US012779106B2

(12) United States Patent
Xiao

(10) Patent No.: US 12,779,106 B2
(45) Date of Patent: Nov. 3, 2026

(54) CLEANER

(71) Applicant: Shenzhen Gaodi Digital Co., Ltd., Shenzhen (CN)

(72) Inventor: Ronghua Xiao, Shenzhen (CN)

(73) Assignee: Shenzhen Gaodi Digital Co., Ltd., Shenzhen (CN)

( * ) Notice: Subject to any disclaimer, the term of this patent is extended or adjusted under 35 U.S.C. 154(b) by 528 days.

(21) Appl. No.: 18/465,554

(22) Filed: Sep. 12, 2023

(65) Prior Publication Data

US 2025/0041506 A1 Feb. 6, 2025

(30) Foreign Application Priority Data

Aug. 3, 2023 (CN) ......................... 202322074767.6

(51) Int. Cl.
*A61M 3/02* (2006.01)
*A61M 11/00* (2006.01)

(52) U.S. Cl.
CPC ........ *A61M 3/0287* (2013.01); *A61M 3/0258* (2013.01); *A61M 11/00* (2013.01); *A61M 2205/8206* (2013.01)

(58) Field of Classification Search
CPC .............. A61M 3/0287; A61M 3/0258; A61M 2205/8206; A61M 3/0279
See application file for complete search history.

(56) References Cited

U.S. PATENT DOCUMENTS

D971,405 S 11/2022 Wang
2003/0168476 A1* 9/2003 Sanchez ................ B65D 83/56 222/321.7
2022/0168496 A1 6/2022 Wagner

* cited by examiner

*Primary Examiner* — Bradley J Osinski

(57) ABSTRACT

Provided is a cleaner, including a sprayer, a switching assembly, a water storage assembly, a conveying assembly, and a housing. Because the switching assembly movably connected to the housing is arranged and the sprayer is fixedly connected to the switching assembly, a position and an angle of the sprayer can be adjusted by moving the switching assembly, such that the use convenience is brought for a user, and a storage groove does not need to be formed, making the cleaner more attractive.

10 Claims, 11 Drawing Sheets

CLEANER

TECHNICAL FIELD

The present application relates to the field of cleaning tools, in particular to a cleaner.

BACKGROUND

In the prior art, some cleaners adopt a storage mode that a sprayer is stored in a groove on an outer side of a housing of a cleaner through folding. However, in such a storage mode, a cleaning head needs to be exposed in an external environment and thus is easily polluted by dust, dirt, and bacteria in the air, and because the groove for storage needs to be formed in the outer side of the housing of the cleaner, the overall design of the cleaner is not simple enough to affect the overall appearance of the cleaner. Sprayers of some cleaners are arranged at the tops thereof, which will cause an issue that the sprayers cannot be adjusted in position and angle. When a user uses the cleaner, the cleaner must be used at a fixed position and at a fixed angle, which easily brings the use inconvenience for the user.

SUMMARY

Based on this, it is necessary to provide a cleaner, to solve at least one of the above problems.

The present application provides a cleaner, including a sprayer, a switching assembly, a water storage assembly, a conveying assembly, and a housing, wherein both the water storage assembly and the conveying assembly are accommodated in the housing, the switching assembly is movably connected to the housing, the sprayer is fixedly connected to the switching assembly, the water storage assembly selectively stores a cleaning solution, the conveying assembly is arranged between the switching assembly and the water storage assembly and drives the cleaning solution in the water storage assembly to move, the switching assembly communicates with the sprayer and the water storage assembly, and the cleaning solution is driven by the conveying assembly to pass through the switching assembly and the sprayer from the water storage assembly and be sprayed from the sprayer.

Optionally, the switching assembly is rotatably connected to the housing.

Optionally, the switching assembly includes a guide member and a first outer support, the housing includes a groove, the guide member is clamped in the groove, and the first outer support is rotatably mounted on the guide member.

Optionally, the switching assembly further includes a shaft assembly, the shaft assembly includes a fixing part and a rotating part, the fixing part is fixedly connected to a surface of the groove that faces the first outer support, the rotating part is arranged between the fixing part and the first outer support and is rotatably connected to the fixing part, and the first outer support is fixedly connected to the rotating part.

Optionally, the switching assembly further includes a first inner support, the first outer support is fixedly connected to the first inner support, and the first inner support is fixedly connected to the rotating part.

Optionally, the first inner support includes a tubular cavity, the switching assembly further includes a tube body, at least part of the tube body is accommodated in the tubular cavity, the housing further includes a first outlet, the first outlet is located between the housing and the tube body and is formed in the groove of the housing, and the tube body has one end communicating with the first outlet and the other end communicating with the sprayer.

Optionally, the tube body includes a first tube body and a second tube body, at least part of the second tube body is accommodated in the tubular cavity, the first tube body has one end communicating with the first outlet and the other end communicating with one end of the second tube body, and the other end of the second tube body communicates with the sprayer.

Optionally, the shaft assembly further includes a sleeve-shaped part, each of the fixing part and the rotating part has a first inner hole, the sleeve-shaped part has a second inner hole, the sleeve-shaped part penetrates through the first inner hole of the fixing part and the first inner hole of the rotating part and is sleeved on an outer side of the tube body through the second inner hole, the fixing part is fixedly connected to the sleeve-shaped part, and the rotating part is rotatably connected to the sleeve-shaped part.

Optionally, the cleaner further includes a first cover, the first cover includes a cavity, one end of the housing that faces the sprayer is provided with an edge, the edge is arranged on a periphery of the guide member, the sprayer has a storage state and a usage state, when the sprayer is in the storage state, the first cover is clamped to the guide member and supported by the edge, and the sprayer is located in a direction of storage and accommodated in the cavity, and when the sprayer is in the usage state, the first cover is dismounted, and the sprayer is rotated to a direction of use by the switching assembly.

Optionally, the tubular cavity has two openings communicating with an interior of the tubular cavity, the two openings are arranged close to the first outlet and the sprayer, respectively, one end of the first tube body extends into the tubular cavity through the opening arranged close to the first outlet, when the sprayer is in the storage state, one end of the second tube body that faces the first tube body abuts against one end of the first tube body that is accommodated in the tubular cavity so that the second tube body fully or partially retracts into the tubular cavity, and when the sprayer is in the usage state, the one end of the second tube body that faces the first tube body moves along the tubular cavity to the vicinity of the opening arranged close to the sprayer so that the second tube body extends from the tubular cavity.

In the above cleaner, because the switching assembly movably connected to the housing is arranged and the sprayer is fixedly connected to the switching assembly, a position and an angle of the sprayer can be adjusted by moving the switching assembly, such that the use convenience is brought for a user, and a storage groove does not need to be formed, making the cleaner more attractive.

BRIEF DESCRIPTION OF THE DRAWINGS

The accompanying drawings are only for illustrative purposes and cannot be understood as a limitation on this patent; and the same reference signs are used for members with the same structure and function. In the drawings.

Description of reference signs: sprayer-1; switching assembly-2; button-3; liquid storage assembly-4; first cover-5; charging assembly-6; conveying assembly-7; housing-8; flexible pad-11; first support holder-12; first bulge-13; first surface-14; third inner hole-15; second outlet-16; spray outlet-17; tube body-20; first outer support-21; third sealing ring-210; first inner support-211; second tube body-212; tubular cavity-213; connecting part-214; first inner hole-215; first inner hole-215; second inner hole-216; first tube body-22; guide member-23; shaft assembly-24; fixing part-25; rotating part-26; first sealing ring-27; sleeve-shaped part-28; second sealing ring-29; second cover-41; cavity-51; first fixing member-81; second fixing member-82; first outlet-83; groove-84; nozzle-85; and edge-86.

DETAILED DESCRIPTION OF THE EMBODIMENTS

The technical solutions in the embodiments of the present application will be described below with reference to the accompanying drawings in the embodiments of the present application. In the description of the embodiments of the present application, unless otherwise specified, "/" means or, for example, A/B may mean A or B; and "and/or" herein is merely intended to describe an association relationship of associated objects, indicating that three relationships may exist, for example, A and/or B may mean that only A, both A and B, or only B exists. In addition, in the description of the embodiments of the present application, "a plurality of" refers to two or more.

Hereinafter, the terms "first" and "second" are only for descriptive purposes, and cannot be construed as indicating or implying relative importance or implying the number of technical features indicated. Thus, the features defined with "first" and "second" may explicitly or implicitly include one or more of the features.

Figure 1:
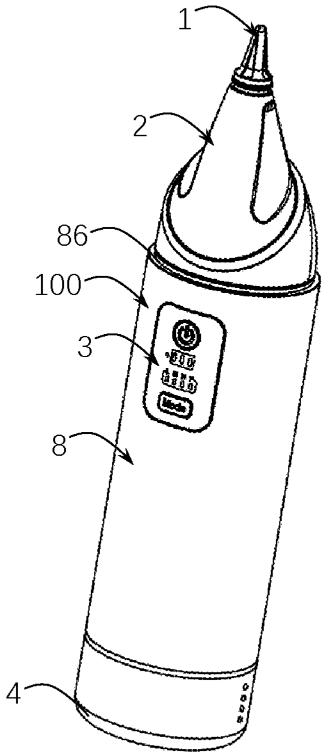
FIG. 1 is a schematic diagram of an overall structure of a cleaner according to an embodiment of the present application.
Figure 2:
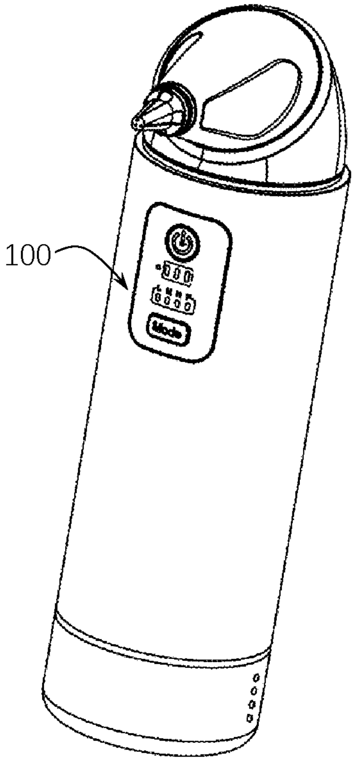
FIG. 2 is a schematic diagram of an overall structure of a cleaner in a usage state according to an embodiment of the present application.
Figure 3:
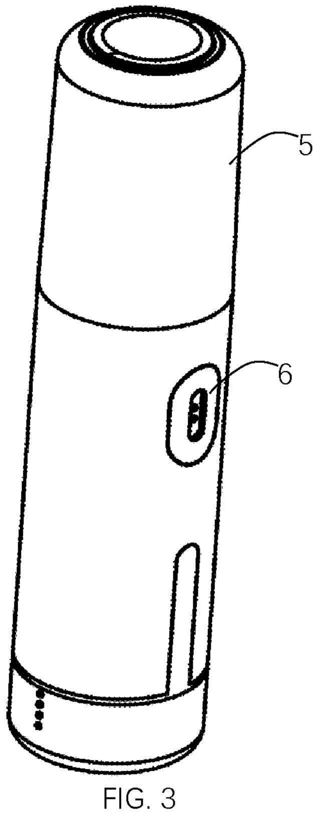
FIG. 3 is a schematic diagram of an overall structure of a cleaner in a storage state according to an embodiment of the present application.
Figure 4:
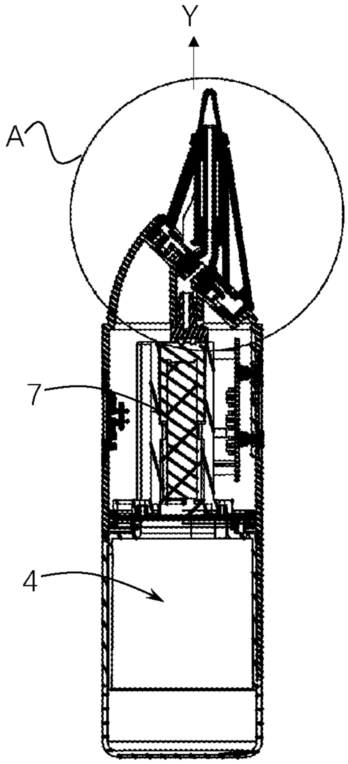
FIG. 4 is a schematic structural sectional view of the cleaner in FIG. 1.
Figure 5:
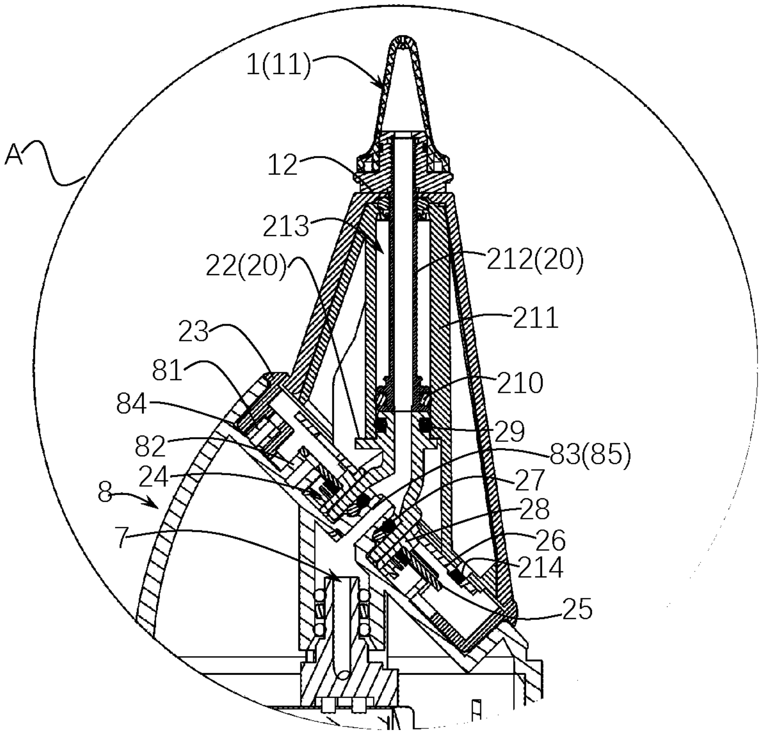
FIG. 5 is a partial enlarged view of A in FIG. 5.
Figure 6:
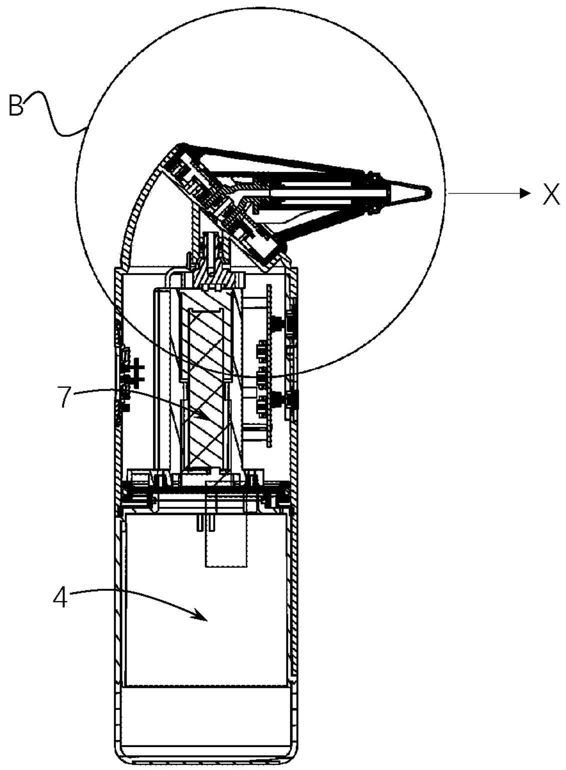
FIG. 6 is a schematic structural sectional view of the cleaner in FIG. 2.
Figure 7:
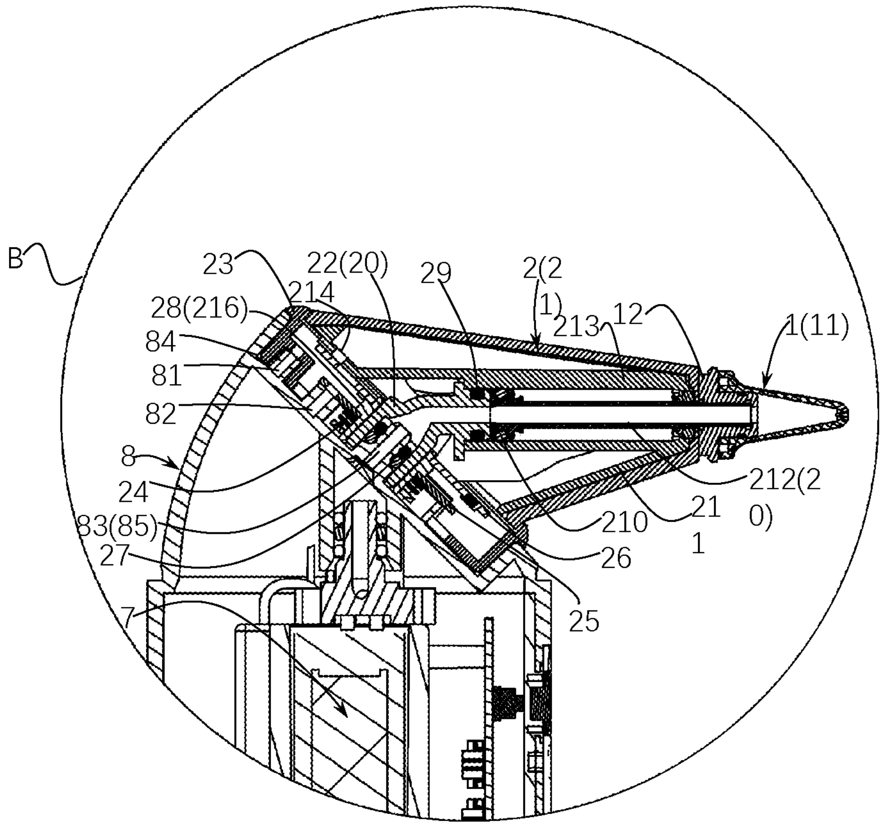
FIG. 7 is a partial enlarged view of B in FIG. 6.
Figure 8:
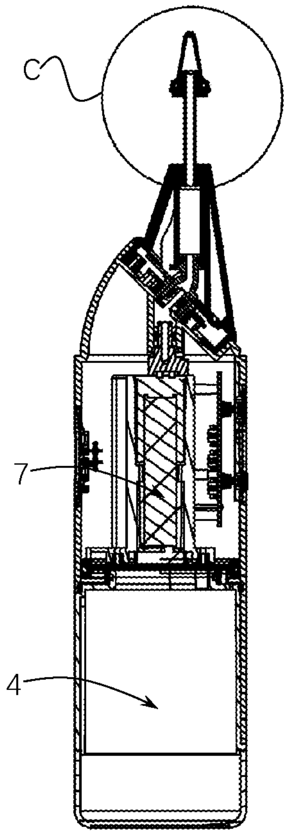
FIG. 8 is a schematic diagram of an overall structure of a cleaner with a sprayer in an extension state according to an embodiment of the present application.
Figure 9:
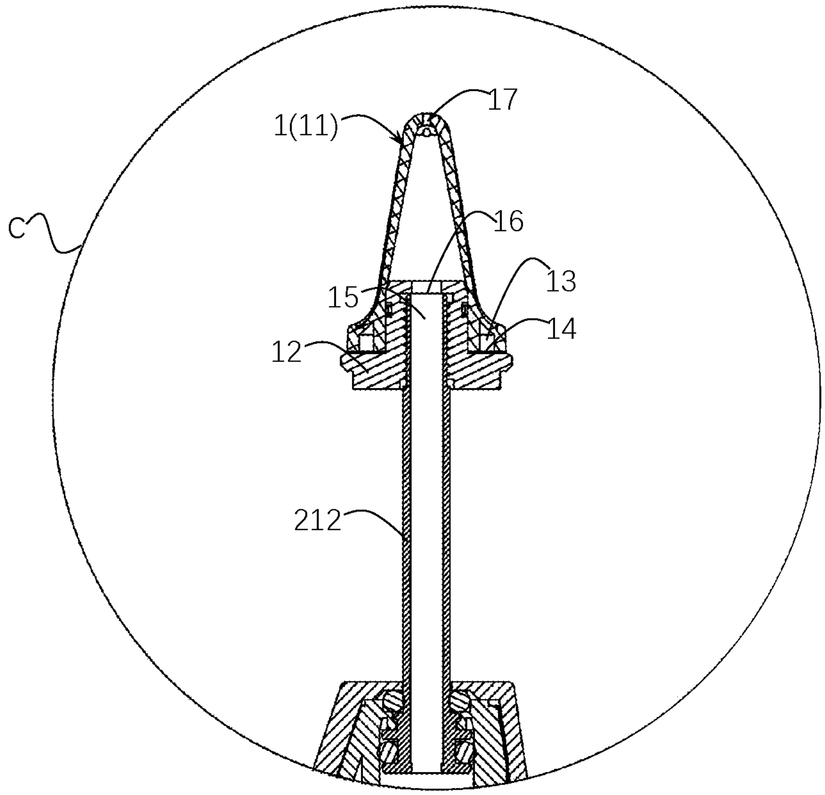
FIG. 9 is a partial enlarged view of C in FIG. 8.
Figure 10:
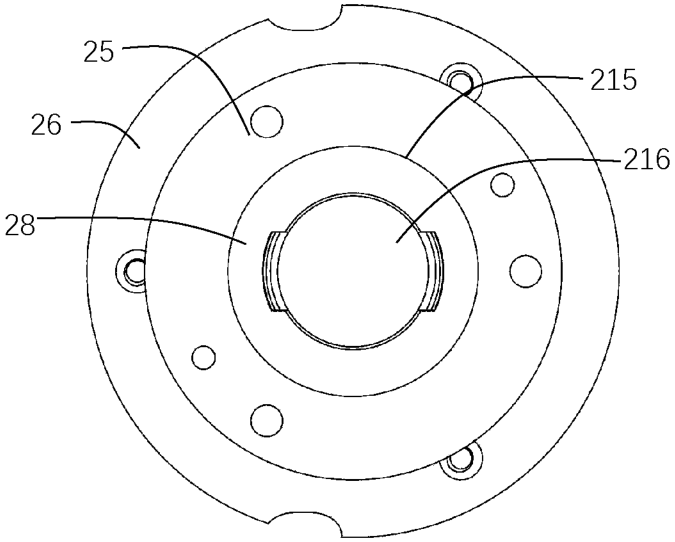
FIG. 10 is a schematic structural top view of a shaft assembly according to an embodiment of the present application.
Figure 11:
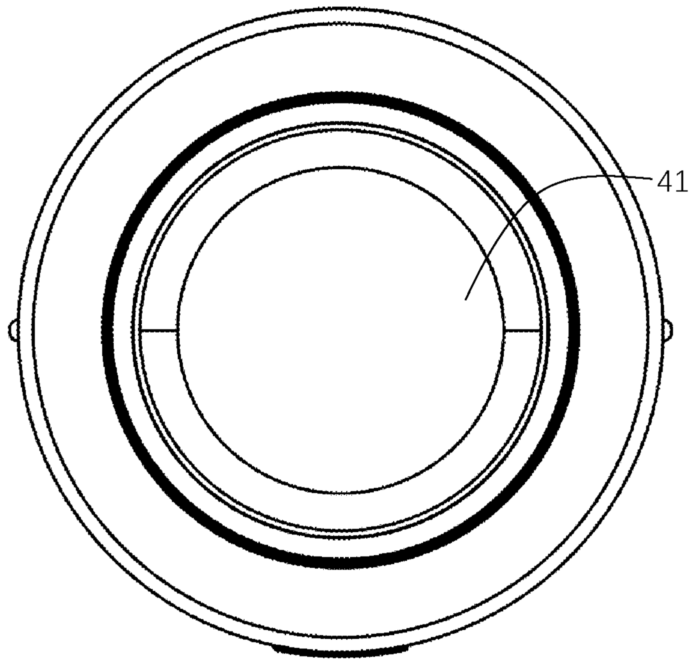
FIG. 11 is a schematic structural bottom view of a cleaner according to an embodiment of the present application.

Referring to FIGS. 1 to 9, in this embodiment, exemplarily, a cleaner 100 includes a sprayer 1, a switching assembly 2, a water storage assembly 4, a conveying assembly 7, and a housing 8, where both the water storage assembly 4 and the conveying assembly 7 are accommodated in the housing 8, the switching assembly 2 is movably connected to the housing 8, the sprayer 1 is fixedly connected to the switching assembly 2, the water storage assembly 4 selectively stores a cleaning solution, the conveying assembly 7 is arranged between the switching assembly 2 and the water storage assembly 4 and drives the cleaning solution in the water storage assembly 4 to move, the switching assembly 2 communicates with the sprayer 1 and the water storage assembly 4, and the cleaning solution is driven by the conveying assembly 7 to pass through the switching assembly 2 and the sprayer 1 from the water storage assembly 4 and be sprayed from the sprayer 1.

Specifically, the switching assembly 2 is rotatably connected to the housing 8, and a position of the switching assembly 2 can be switched by rotating the switching assembly 2, so as to switch a position of the sprayer 1 fixed to the switching assembly 2.

Specifically, the switching assembly 2 includes a guide member 23 and a first outer support 21, the housing 8 includes a groove 84, the guide member 23 is clamped in the groove 84, and the first outer support 21 is rotatably mounted on the guide member 23.

Further, the guide member 23 is of an annular structure, an annular groove 84 arranged along a circumferential direction of the annular structure is provided on a surface of the annular structure that faces the first outer support 21, and a part of the first outer support 21 that faces the annular groove 84 is matched in shape with the annular groove 84, such that the part of the first outer support 21 that faces the annular groove 84 can slide along the annular groove 84, and thus the first outer support 21 can rotate around the annular groove 84. In this way, due to the arrangement of the guide member 23 for guidance, the first outer support 21 can rotate more stably.

Specifically, the switching assembly 2 further includes a shaft assembly 24, the shaft assembly 24 includes a fixing part 25 and a rotating part 26, the fixing part 25 is fixedly connected to a surface of the groove 84 that faces the first outer support 21, the rotating part 26 is arranged between the fixing part 25 and the first outer support 21 and is rotatably connected to the fixing part 25, and the first outer support 21 is fixedly connected to the rotating part 26. In this way, the rotating part 26 can be driven by the first outer support 21 to rotate by rotating the first outer support 21.

Specifically, the switching assembly 2 further includes a first inner support 211, the first outer support 21 is fixedly connected to the first inner support 211, and the first inner support 211 is fixedly connected to the rotating part 26. In this way, the first inner support 211 can be driven by the first outer support 21 to rotate by rotating the first outer support 21, and the rotating part 26 can be driven by the first inner support 211 to rotate.

Specifically, the first outer support 21 is arranged between the first inner support 211 and the sprayer 1 and is sleeved on the first inner support 211, a part of an outer side surface of the first inner support 211 that faces the sprayer 1 is provided with a clamping groove, a part of an inner side surface of the first outer support 21 that faces the clamping groove is provided with a bulge, the bulge is clamped in the clamping groove and restricts the first inner support 211 from moving towards the sprayer 1, a part of an outer side surface of the first outer support 21 that faces the annular groove 84 is matched in shape with the annular groove 84, the first outer support 21 can slide along the annular groove 84, the annular groove 84 restricts the first outer support 21 from moving in a direction of the annular groove 84, the first inner support 211 is fixedly connected to the rotating part 26, and the rotating part 26 restricts the first outer support 21 from moving towards the rotating part 26. In this way, because the first outer support 21 is restricted from moving in a plurality of directions, the first outer support 21 can be fixed to the first inner support 211.

Specifically, the cleaner further includes a first cover 5, the first cover 5 includes a cavity 51, one end of the housing 8 that faces the sprayer 1 is provided with an edge 86, the edge 86 is arranged on a periphery of the guide member 23, the sprayer 1 has a storage state and a usage state, when the sprayer 1 is in the storage state, the first cover 5 is clamped to the guide member 23 and supported by the edge 86, and the sprayer 1 is located in a direction of storage and accommodated in the cavity 51, and when the sprayer 1 is in the usage state, the first cover 5 is dismounted, and the sprayer 1 is rotated to a direction of use by the switching assembly 2. In this way, because the sprayer 1 is selectively rotated to the direction of storage and the direction of use by the switching assembly 2, when a user holds the housing 8 to use the cleaner, an axis of the housing 8 of the cleaner is usually in a vertical direction, and the sprayer 1 and the axis of the housing 8 form a certain angle, which is the direction of use, such that the user can conveniently align the sprayer 1 with a part that needs to be cleaned; and when the user does not use the cleaner, the user can rotate the first outer support 21 to rotate the first inner support 211 and then rotate the rotating part 26 to adjust the sprayer 1 to the direction of storage, such that the sprayer 1 can be fully accommodated in a storage cavity of the first cover 5.

Understandably, in some embodiments, the switching assembly 2 is translationally connected to the housing 8, and the position of the switching assembly 2 can be switched by rotating the switching assembly 2, so as to switch the position of the sprayer 1 fixed to the switching assembly 2.

Specifically, the first inner support 211 includes a tubular cavity 213, the switching assembly 2 further includes a tube body 20, at least part of the tube body 20 is accommodated in the tubular cavity 213, the housing 8 further includes a first outlet 83, the first outlet 83 is located between the housing 8 and the tube body 20 and is formed in the groove 84 of the housing 8, and the tube body 20 has one end communicating with the first outlet 83 and the other end communicating with the sprayer 1. In this way, because the at least part of the tube body 20 is accommodated in the tubular cavity 213, the tubular cavity 213 can drive the tube body 20 to move.

Specifically, the tube body 20 includes a first tube body 22 and a second tube body 212, at least part of the second tube body 212 is accommodated in the tubular cavity 213, the first tube body 22 has one end communicating with the first outlet 83 and the other end communicating with one end of the second tube body 212, and the other end of the second tube body 212 communicates with the sprayer 1.

Specifically, the first tube body 22 is a flexible tube, and the second tube body 212 is a hard tube. In this way, because the first tube body 22 is the flexible tube, when one end of the first tube body 22 that is connected to the second tube body 212 moves with the second tube body 212, the first tube body 22 can flexibly change its shape, thereby avoiding the problem of fracture failure of the first tube body 22 due to the movement of the second tube body 212, and avoiding the restriction of the movement of the second tube body 212 due to the restriction of the shape of the first tube body 22; and because the second tube body 212 is the hard tube, the second tube body 212 is more stably mounted in the tubular cavity 213 of the first inner support 211, such that when the first inner support 211 moves, the tubular cavity 213 can more stably drive the second tube body 212 to move.

Specifically, the tubular cavity 213 has two openings communicating with an interior of the tubular cavity 213; the two openings are arranged close to the first outlet 83 and the sprayer 1, respectively; one end of the first tube body 22 extends into the tubular cavity 213 through the opening arranged close to the first outlet 83; when the sprayer 1 is in the storage state, one end of the second tube body 212 that faces the first tube body 22 abuts against one end of the first tube body 22 that is accommodated in the tubular cavity 213 so that the second tube body 212 fully or partially retracts into the tubular cavity 213, the sprayer 1 abuts against one end of the first outer support 21 that faces the sprayer 1 and one end of the first inner support 211 that faces the sprayer 1, and the sprayer 1 is in a retraction state; and when the sprayer 1 is in the usage state, the one end of the second tube body 212 that faces the first tube body 22 moves along the tubular cavity 213 to the vicinity of the opening arranged close to the sprayer 1 so that the second tube body 212 extends from the tubular cavity 213, and the sprayer 1 is in an extension state. In this way, because the second tube body 212 is telescopic relative to the opening arranged close to the sprayer 1, when holding the housing 8 to use the cleaner, a user can adjust a spraying position of the sprayer 1 as needed, such that the user can adjust the position and angle of the sprayer simultaneously and thus can use the cleaner more conveniently.

Specifically, a bottom of the second tube body 212 is provided with a bulge, a spring piece is arranged near the opening arranged close to the sprayer 1, a clamping position is arranged on the spring piece, and when one end of the second tube body 212 that faces the first tube body 22 moves along the tubular cavity 213 to the vicinity of the opening arranged close to the sprayer 1 so that the second tube body 212 extends from the tubular cavity 213, the bulge pushes away the spring piece and is clamped in the clamping position on the spring piece. In this way, when extending from the tubular cavity 213 to a suitable position, the second tube body 212 can be fixed in the position by the bulge and the clamping position, such that the user can use the cleaner more stably.

The first inner support 211 further includes a connecting part 214 connected to the rotating part 26 by a bolt. In this way, the first inner support 211 can be fixedly connected to the rotating part 26.

Specifically, the groove 84 of the housing 8 is arranged opposite to the first inner support 211, a surface of the groove 84 of the housing 8 that faces the first inner support 211 is provided with a nozzle 85 protruding towards one side where the first inner support 211 is located, the first outlet 83 is formed in the nozzle 85 and communicates with the conveying assembly 7, and one end of the first tube body 22 is sleeved on a periphery of the nozzle 85. In this way, the first tube body 22 can be more stably connected to the first outlet 83.

Specifically, the shaft assembly 24 further includes a sleeve-shaped part 28, each of the fixing part 25 and the rotating part 26 has a first inner hole 215, the sleeve-shaped part 28 has a second inner hole 216, the sleeve-shaped part 28 penetrates through the first inner hole 215 of the fixing part 25 and the first inner hole 215 of the rotating part 26 and is sleeved on an outer side of the tube body 20 through the second inner hole 216, the fixing part 25 is fixedly connected to the sleeve-shaped part 28, and the rotating part 26 is rotatably connected to the sleeve-shaped part 28. In this way, because the sleeve-shaped part 28 sleeved on the outer side of the tube body 20 is arranged and fixed to the fixing part 25, the rotating part 26 does not damage the tube body 20 during rotation.

Specifically, the sleeve-shaped part 28 has a bulge located between the fixing part 25 and the rotating part 26, and the bulge separates the fixing part 25 from the rotating part 26.

Specifically, the nozzle 85 and the first tube body 22 sleeved on the periphery of the nozzle 85 are sealed with a first sealing ring 27.

Specifically, the first tube body 22 and the tubular cavity 213 are sealed with a second sealing ring 29.

Specifically, one end of the second tube body 212 that abuts against the first tube body 22 is located in the tubular cavity 213, and the tubular cavity 213 and the second tube body 212 are sealed with a third sealing ring 210.

Specifically, the housing 8 includes a first fixing member 81, and the guide member 23 is fixed to the first fixing member 81.

Specifically, the first fixing member 81 is a threaded hole, the guide member 23 has a threaded hole, and a bolt penetrates through the threaded hole to fix the guide member 23 in the groove 84 of the housing 8.

Specifically, the housing 8 further includes a second fixing member 82, and the fixing part 25 is fixed to the second fixing member 82.

Specifically, the second fixing member 82 is a threaded hole, the fixing part 25 has a threaded hole, and a bolt penetrates through the threaded hole to fix the fixing part 25 in the groove 84 of the housing 8.

Specifically, there may be two, three, four or other number of first fixing elements 81 and second fixing members 82, but is not limited to this.

Specifically, the liquid storage assembly 4 is arranged in the housing 8 and includes a liquid storage cavity and a second cover 41, the liquid storage cavity is configured to store the cleaning solution, the second cover 41 is selectively connected to the housing 8 in an open state and a closed state, when the second cover 41 is in the open state, the liquid storage assembly 4 can be injected with a new cleaning solution and can be cleaned from outside, and when the second cover 41 is in the closed state, the liquid storage assembly 4 stores the cleaning solution.

Specifically, the second cover 41 is arranged at one end of the housing 8 that deviates from the sprayer 1, an injection hole is formed in the housing 8 and communicates with the liquid storage cavity, and the second cover 41 is openably connected to a position of the housing 8 that is near the injection hole by a hinge.

Specifically, the conveying assembly 7 communicates with the switching assembly 2 and the liquid storage assembly 4, and the conveying assembly 7 drives the cleaning solution in the liquid storage assembly 4 to move to the switching assembly 2. Understandably, in some embodiments, the liquid storage assembly 4 may also directly communicate with the switching assembly 2, and the conveying assembly 7 only generates a driving force on the cleaning solution in the liquid storage assembly 4 so that the cleaning solution enters the switching assembly 2.

Specifically, the conveying assembly 7 includes a pump and a conveying channel, the conveying channel communicates with the liquid storage cavity and the first outlet 83, and the pump generates a negative pressure in the conveying channel or a positive pressure in the liquid storage cavity, so as to drive the cleaning solution to enter the conveying channel from the liquid storage cavity and flow out of the first outlet 83.

Specifically, the conveying assembly 7 further includes a valve arranged at the conveying channel to control the opening and closing of the conveying channel.

Specifically, the cleaner further includes a button 3, and the button 3 includes a power button. Understandably, in some embodiments, there are a plurality of buttons 3, and other buttons 3 may be a button 3 for controlling the opening or closing of the valve, a button 3 for controlling the opening or closing of the first cover 5, a button 3 for controlling the opening or closing of the second cover 41, etc., but are not limited to this.

Specifically, the pump of the cleaner is powered by a rechargeable battery, and the cleaner further includes a charging assembly 66 connected to the rechargeable battery to charge the rechargeable battery. Understandably, in some embodiments, the pump of the cleaner may also be powered by an ordinary battery, a USB socket, a plug, etc., but is not limited to this.

Specifically, the sprayer 1 includes a flexible pad 11, a first support holder 12, and a first bulge 13, the first support holder 12 includes a third inner hole 15, the first support holder 12 is sleeved on a periphery of the tube body 20 through the third inner hole 15, the flexible pad 11 is arranged at the second outlet 16 of the tube body 20 and mounted on the first support holder 12, one side of the first support holder 12 that faces the flexible pad 11 is provided with a first surface 14, the first bulge 13 is arranged on the first surface 14, a groove is formed in a position of the flexible pad 11 that corresponds to the first bulge 13, the first bulge 13 of the flexible pad 11 is clamped in the groove, and the flexible pad 11 has a spray outlet 17 arranged opposite to the second outlet 16.

A process of using the cleaner is as follows:

The user dismounts the first cover 5 and pulls the first outer support 21 to rotate so that the first inner support 211 is driven to rotate and then the rotating part 26 is driven to rotate to adjust the sprayer 1 to the direction of use, the user pulls out the sprayer 1 and turns on the power button, the pump of the cleaner works to generate the negative pressure at the conveying channel, the valve is opened, and the cleaning solution is driven from the liquid storage cavity to the conveying channel, then is conveyed to the nozzle 85 of the housing 8, next is conveyed to the first tube body 22 and the second tube body 212, and finally is conveyed to the sprayer 1 to be sprayed towards the part to be cleaned of the user.

A process of storing the cleaner is as follows:

The user presses the sprayer 1 to abut against one end of the first outer support 21 that faces the sprayer 1 and one end of the first inner support 211 that faces the sprayer 1, the user pulls the first outer support 21 to rotate so that the first inner support 211 is driven to rotate and then the rotating part 26 is driven to rotate to adjust the sprayer 1 to the direction of storage, the user mounts the first cover 5, and the user turns off the power button.

In the description of this embodiment, "a plurality of" means two or more, unless otherwise stated. The above contents are only specific embodiments of the present application, but the scope of protection of the present application is not limited thereto. Any changes or substitutions within the technical scope of the present application should all be included in the scope of protection of the present application. Therefore, the scope of protection of the present application should be subject to the scope of protection of the claims.

What is claimed is:

1. A cleaner, comprising a sprayer, a switching assembly, a water storage assembly, a conveying assembly, and a housing, wherein both the water storage assembly and the conveying assembly are accommodated in the housing, the switching assembly is movably connected to the housing, the sprayer is fixedly connected to the switching assembly, the water storage assembly selectively stores a cleaning solution, the conveying assembly is arranged between the switching assembly and the water storage assembly and drives the cleaning solution in the water storage assembly to move, the switching assembly communicates with the sprayer and the water storage assembly, and the cleaning solution is driven by the conveying assembly to pass through the switching assembly and the sprayer from the water storage assembly and be sprayed from the sprayer; and wherein the switching assembly comprises a first outer support and a first inner support, the first outer support is fixedly connected to the first inner support, the first inner support comprises a tubular cavity, the switching assembly comprises a tube body, at least part of the tube body is accommodated in the tubular cavity, the housing comprises a first outlet in communication with the conveying assembly, and the tube body has one end communicating with the first outlet and another end communicating with the sprayer.

2. The cleaner according to claim 1, wherein the switching assembly is rotatably connected to the housing.

3. The cleaner according to claim 2, wherein the switching assembly further comprises a guide member, the housing comprises a groove, the guide member is clamped in the groove, and the first outer support is rotatably mounted on the guide member.

4. The cleaner according to claim 3, wherein the switching assembly further comprises a shaft assembly, the shaft assembly comprises a fixing part and a rotating part, the fixing part is fixedly connected to a surface of the groove that faces the first outer support, the rotating part is arranged between the fixing part and the first outer support and is rotatably connected to the fixing part, and the first outer support is fixedly connected to the rotating part.

5. The cleaner according to claim 4, wherein the first inner support is fixedly connected to the rotating part.

6. The cleaner according to claim 4, wherein the shaft assembly further comprises a sleeve-shaped part, each of the fixing part and the rotating part has a first inner hole, the sleeve-shaped part has a second inner hole, the sleeve-shaped part penetrates through the first inner hole of the fixing part and the first inner hole of the rotating part and is sleeved on an outer side of the tube body through the second inner hole, the fixing part is fixedly connected to the sleeve-shaped part, and the rotating part is rotatably connected to the sleeve-shaped part.

7. The cleaner according to claim 1, wherein the tube body comprises a first tube body and a second tube body, at least part of the second tube body is accommodated in the tubular cavity, the first tube body has one end communicating with the first outlet and another end communicating with one end of the second tube body, and another end of the second tube body communicates with the sprayer.

8. The cleaner according to claim 7, further comprising a first cover, wherein the first cover comprises a cavity, one end of the housing that faces the sprayer is provided with an edge, the edge is arranged on a periphery of the guide member, the sprayer has a storage state and a usage state, when the sprayer is in the storage state, the first cover is clamped to the guide member and supported by the edge, and the sprayer is located in a direction of storage and accommodated in the cavity, and when the sprayer is in the usage state, the first cover is dismounted, and the sprayer is rotated to a direction of use by the switching assembly.

9. The cleaner according to claim 8, wherein the tubular cavity has two openings communicating with an interior of the tubular cavity, the two openings are arranged close to the first outlet and the sprayer, respectively, one end of the first tube body extends into the tubular cavity through the opening arranged close to the first outlet, when the sprayer is in the storage state, one end of the second tube body that faces the first tube body abuts against one end of the first tube body that is accommodated in the tubular cavity so that the second tube body fully or partially retracts into the tubular cavity, and when the sprayer is in the usage state, the one end of the second tube body that faces the first tube body moves along the tubular cavity to the vicinity of the opening arranged close to the sprayer so that the second tube body extends from the tubular cavity.

10. The cleaner according to claim 1, wherein the first inner support is disposed within the first outer support.

* * * * *